US012767633B2

(12) United States Patent
Moloney et al.

(10) Patent No.: US 12,767,633 B2
(45) Date of Patent: Oct. 20, 2026

(54) SULFIDE-BASED COMPOUNDS AND USES THEREOF

(71) Applicant: Ecolab USA Inc., St. Paul, MN (US)

(72) Inventors: Jeremy Moloney, Katy, TX (US); Ashish Dhawan, Aurora, IL (US); Carter Silvernail, Lakeville, MN (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 18/631,753

(22) Filed: Apr. 10, 2024

(65) Prior Publication Data

US 2024/0270687 A1 Aug. 15, 2024

Related U.S. Application Data

(62) Division of application No. 16/593,212, filed on Oct. 4, 2019, now Pat. No. 11,981,625.

(60) Provisional application No. 62/742,651, filed on Oct. 8, 2018.

(51) Int. Cl.

| | |
|---|---|
| ***C07C 323/25*** | (2006.01) |
| ***C07C 319/04*** | (2006.01) |
| ***C07D 213/32*** | (2006.01) |
| ***C09K 8/54*** | (2006.01) |

(52) U.S. Cl.

CPC .......... *C07C 323/25* (2013.01); *C07D 213/32* (2013.01); *C09K 8/54* (2013.01); *C07C 319/04* (2013.01); *C09K 2208/32* (2013.01)

(58) Field of Classification Search

CPC ........................................................ C09K 8/54

See application file for complete search history.

(56) References Cited

U.S. PATENT DOCUMENTS

| | | | |
|---|---|---|---|
| 2,607,776 | A | 8/1952 | Vinten |
| 3,409,626 | A | 11/1968 | Cavallito et al. |
| 4,231,956 | A | 11/1980 | Sullivan, III et al. |
| 4,246,263 | A | 1/1981 | Lombardino et al. |
| 4,332,967 | A | 6/1982 | Thompson et al. |
| 4,535,084 | A | 8/1985 | Lombardino et al. |
| 2002/0107151 | A1 | 8/2002 | Ahn et al. |
| 2006/0041145 | A1 | 2/2006 | Hayashi et al. |
| 2013/0101460 | A1 | 4/2013 | Ramachandran et al. |
| 2016/0009642 | A1* | 1/2016 | Wu ........................ A61K 31/22 514/544 |
| 2017/0014528 | A1* | 1/2017 | Sengupta ......... A61K 47/68037 |
| 2017/0342310 | A1 | 11/2017 | Obeyesekere et al. |
| 2017/0355846 | A1 | 12/2017 | Huang et al. |

FOREIGN PATENT DOCUMENTS

| | | | |
|---|---|---|---|
| CN | 105801456 | A | 7/2016 |
| CN | 107501480 | A | 12/2017 |
| DE | 2933388 | A1 | 3/1981 |
| EP | 0154296 | A2 | 9/1985 |
| GB | 842995 | | 8/1960 |
| WO | 97/12076 | A1 | 4/1997 |
| WO | 0112878 | A1 | 2/2001 |
| WO | 2015017385 | A2 | 2/2015 |
| WO | 2017087055 | A1 | 5/2017 |
| WO | 2018102724 | A1 | 6/2018 |

OTHER PUBLICATIONS

Nilsson et al. (2007) "Addition of Thiol-Containing Ligands to a Surface-Active Michael Acceptor", Macromolecules, 40(4):901-908.

Barker et al. (2014) "General Corrosion of X65 Steel under Silica Sand Deposits in CO2-Saturated Environments in the Presence of Corrosion Inhibitor Components", Corrosion, Paper No. 4215:1-19.

Abrouki et al. (2013) "Sodium Pyrophosphate: A Novel and Efficient Catalyst for Sulfa-Michael additions", American Journal of Biological, Chemical and Pharmaceutical Sciences, 1(5):16-21.

Rana et al. (2010) "Highly Enantioselective Organocatalytic Sulfa-Michael Addition to α, β-Unsaturated Ketones", J. Org. Chem., 75(6):1-23.

Movassagh et al. (2006) "Michael addition of thiols to α, β—unsaturated carbonyl compounds under solvent-free conditions", Arkivoc, General Papers, (xii):130-137.

Kolb et al. (2001) "Click Chemistry: Diverse Chemical Function from a Few Good Reactions", Angew. Chem. Int. Ed., 40:2004-2021.

Yang et al. (2017) "Enantioselective bifunctional iminophosphorane catalyzed sulfa-Michael addition of alkyl thiols to unactivated β-substituted-α, β-unsaturated esters", Chemical Science, 8:606-610.

Bouklah et al. "Corrosion inhibition of steel in 0.5 M H2SO4 by [(2-pyridin-4-ylethyl)thio]acetic acid", Applied Surface Science, 2005, vol. 250, pp. 50-56.

Krim et al. "Synthesis, Characterization, and Comparative Study of Pyridine Derivatives as Corrosion Inhibitors of Mild Steel in HCl Medium" Chem. Eng. Comm., 2009, vol. 196, pp. 1536-1546.

Beloglazov et al. "Corrosion Behaviour of Steel in Coal Mining Water in the Presence of Thiobacillus thiooxidans and Thiobacillus u ferrooxidans" Microbial Corrosion: Proceedings of the 3rd International EFC Workshop 1994, pp. 398-404.

English machine translation of Yonekura et al. WO 97/12076A1, 1997.

English machine translation of DE 2933388 A1, 1981.

Garg et al., (2005) "Copper(II) tetrafluoroborate as a novel and highly efficient catalyst for Michael addition of rnercaptans to a, JI-unsaturated carbonyl compounds", Tetrahedron Letters, 46:1721-1724.

* cited by examiner

*Primary Examiner* — Peter F Godenschwager
(74) *Attorney, Agent, or Firm* — Kagan Binder, PLLC

(57) ABSTRACT

Disclosed are sulfide-based compounds which are a product of a Michael addition reaction between a sulfur-containing donor group and an unsaturated hydrocarbon moiety. The sulfide-based compounds may be used in compositions and methods for inhibiting corrosion.

18 Claims, No Drawings

SULFIDE-BASED COMPOUNDS AND USES THEREOF

CROSS REFERENCE TO RELATED APPLICATIONS

This application is a divisional of U.S. patent application Ser. No. 16/593,212, filed on Oct. 4, 2019, which claims priority to U.S. Provisional Patent Application Ser. No. 62/742,651 filed Oct. 8, 2018, the disclosures of which are incorporated herein by reference in their entireties.

BACKGROUND

Corrosion of metal surfaces continues to be a problem in industrial systems such as the oil and gas industry. In the oil and gas industry, aqueous liquids are injected into the earth and can also be recovered from the earth during subterranean hydrocarbon recovery processes such as hydraulic fracturing (fracking) and tertiary oil recovery. In one or more such processes, an aqueous liquid called an "injectate" is injected into a subterranean formation. Injectates include water and entrained solids or solvents therein or both. In one or more such processes a water source called "produced water," namely water that flows back from the subterranean formation, is recovered and collected. Produced water includes one or more of injectate, connate (native water present in the subterranean formation along with the hydrocarbon), sea water, and minor (e.g. less than 5 wt. %) amounts of hydrocarbon products, which are hydrocarbon liquids or solids entrained (dispersed, emulsified, or dissolved) in the produced water. The injectate and the produced water can include "corrodents" such as salts, other dissolved solids, liquids, gases or combinations thereof that cause, accelerate, or promote corrosion of metal containments that contact the corrodents. These aggressive constituents can cause severe corrosion as evidenced by surface pitting, embrittlement, and general loss of metal. Corrosion problems are even more troublesome in deep-sea operations where replacement of corroded equipment is difficult and costly. As a result, almost all operators in the oil and gas industry employ corrosion inhibitors to reduce corrosion in metal containments, which contact liquids containing corrodents.

A variety of metal corrosion inhibiting formulations that have been developed including mercaptans. But mercaptans of relatively low molecular weight (for example, methyl mercaptan, ethyl mercaptan, and propyl mercaptan) have low volatility and tend to vaporize and have offensive odors creating problems in and around storage areas and throughout pipelines and shipping systems used for transporting the hydrocarbon.

In view of these challenges, improved corrosion inhibitors are desirable.

SUMMARY

Described herein are compositions that result from a Michael addition reaction.

In one aspect of the invention is a composition comprising at least one sulfide-based compound, the at least one one sulfide-based compound formed by a Michael addition reaction between a sulfa Michael donor and an olefin as a Michael acceptor.

In one aspect of the invention is a fluid source comprising one or more corrodents and at least one sulfide-based.

In another aspect of the invention is a composition comprising a sulfide-based compound comprising the formula:

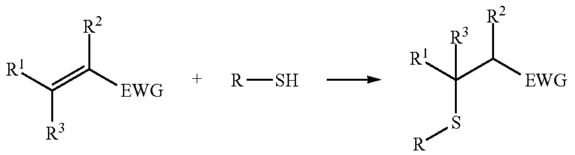

Wherein $R^1$=H or CH3;

$R^2$=H, CH3, an unsubstituted, linear or branched C2 to C30 alkyl, alkenyl, or alkynyl group;

$R^3$=H or CH3

$R^1$, $R^2$, $R^3$=the same or different compounds having ethylenic unsaturations between carbon atoms at the α and β positions relative to an EWG group;

EWG=an electron withdrawing group that is ketone, halo, carbonyl (—CO), nitro (—$NO_2$), nitrile (—CN), alkoxycarbonyl (—COOR), phosphonate (—PO$(OR)_2$), trifluoromethyl (—$CF_3$), sulfonyl (—$SO_2$—), trifluormethanesulfonyl (—$SO_2CF_3$), or p-toluenesulfonyl (—$SO_2$—$C_6H_4$—$CH_3$); and R=straight, branched, cyclic or heterocyclic alkylene, arylene, alkylarylene, arylalkylene, or hydrocarbon moiety having from C1 to C30 carbon atoms.

In still other aspects of the invention is a method of inhibiting corrosion of metal containments in contact with a fluid source comprising the steps of:

introducing into the fluid source a composition comprising at least one sulfide-based compound, the at least one sulfide-based compound formed by a Michael addition reaction between a sulfa Michael donor and an olefin Michael acceptor.

In one aspect of the invention is a treated metal containment comprising a metal containment comprising a metal surface; and the fluid source comprising a sulfide-based compound, wherein at least a portion of the metal surface is contacted by the fluid source.

The above-described compositions and methods are suitable for inhibiting corrosion in many industrial systems such as the oil and gas industry, mining, paper and pulp, wastewater and food processing systems.

DETAILED DESCRIPTION

Although the present disclosure provides references to various embodiments, persons skilled in the art will recognize that changes may be made in form and detail without departing from the spirit and scope of the invention. Reference to various embodiments does not limit the scope of the claims attached hereto. Additionally, any examples set forth in this specification are not intended to be limiting and merely set forth some of the many possible embodiments for the appended claims.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety.

As used herein, the term "aliphatic" or "aliphatic group" refers to a straight-chain or branched hydrocarbon chain that is completely saturated or that contains one or more units of unsaturation, or a monocyclic hydrocarbon or bicyclic hydrocarbon that is completely saturated or that contains one or more units of unsaturation, but which is not aromatic.

As used herein, the term "corrodents," are materials that cause, initiate, catalyze, accelerate, induce, or otherwise promote the corrosion of metals.

As used herein, the term "corrosion inhibitor" means a compound or mixture that prevents, retards, mitigates, reduces, controls and/or delays corrosion.

As used herein, the term "fluid source" means any fluid used in oil or gas well production operations.

As used herein, the term "inhibits," "inhibiting," or grammatical equivalents thereof when used in the context of corrosion inhibition refers to preventing, retarding, mitigating, reducing, controlling and/or delaying corrosion.

As used herein, the term "injectate" means water plus any solids or liquids dispersed therein that is injected into a subterranean formation for the purpose of inducing hydrocarbon recovery therefrom. Injectates optionally include salts, polymers, surfactants, scale inhibitors, stabilizers, metal chelating agents, corrosion inhibitors, paraffin inhibitors, and other additives as determined by the operator in a subterranean hydrocarbon recovery process.

As used herein, the term "olefin" means straight-chain, branched, or cyclic hydrocarbon groups containing two to about 30 carbon atoms and at least one carbon-carbon double bond and derivatives thereof. The olefin can be unsubstituted or substituted with one or more functional groups including alcohol groups, carboxylate groups, and carboxylic acid ester groups.

As used herein, the term "produced water" means water that flows back from a subterranean reservoir and is collected during a hydrocarbon recovery process including, but not limited to hydraulic fracturing and tertiary oil recovery. Produced water includes residual hydrocarbon products entrained therein and one or more of injectate, connate (native water present in the subterranean formation along with the hydrocarbon), brackish water, and sea water. Produced water ranges in temperature from about −30° C. to about 200° C., depending on the subterranean reservoir and the terranean environment and infrastructure proximal to the subterranean reservoir.

As used herein, the terms "mercapto" or "thiol" refer to an —SH substituent, or are used to designate a compound having an —SH substituent.

As used herein, the terms "comprise(s)," "include(s)," "having," "has," "can," "contain(s)," and variants thereof are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "optional" or "optionally" means that the subsequently described event or circumstance may, but need not occur, and that the description includes instances where the event or circumstance occurs and instances in which it does not.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe a range of values, for example "about 1 to 5" the recitation means "1 to 5" and "about 1 to about 5" and "1 to about 5" and "about 1 to 5" unless specifically limited by context.

As used herein, the term "substantially" means "consisting essentially of" and includes "consisting of," and these terms are construed as in U.S. patent law. For example, a solution that is "substantially free" of a specified compound or material may be free of that compound or material, or may have a minor amount of that compound or material present, such as through unintended contamination, side reactions, or incomplete purification. A "minor amount" may be a trace, an unmeasurable amount, an amount that does not interfere with a value or property, or some other amount as provided in context. A composition that has "substantially only" a provided list of components may consist of only those components, or have a trace amount of some other component present, or have one or more additional components that do not materially affect the properties of the composition. Additionally, "substantially" modifying, for example, the type or quantity of an ingredient in a composition, a property, a measurable quantity, a method, a value, or a range, employed in describing the embodiments of the disclosure, refers to a variation that does not affect the overall recited composition, property, quantity, method, value, or range thereof in a manner that negates an intended composition, property, quantity, method, value, or range. Where modified by the term "substantially" the claims appended hereto include equivalents according to this definition.

As used herein, any recited ranges of values contemplate all values within the range and are to be construed as support for claims reciting any sub-ranges having endpoints which are real number values within the recited range. By way of example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

Described herein are compositions and methods directed to sulfide-based compounds. The sulfide-based compounds result from sulfa-Michael addition reactions. The sulfa-Michael addition reactions are between a sulfur-containing group and an unsaturated hydrocarbon moiety (e.g., C═C double bond) that is in proximity of an electron withdrawing group (EWG) such as carbonyl, cyano, or nitro. The Michael addition, generally, is a reaction between nucleophiles and olefin and alkene functionalities, wherein the nucleophile adds across a carbon-carbon multiple bond that is adjacent to an EWG and resonance stabilizing activating group, such as a carbonyl group. The Michael addition nucleophile is known as the "Michael donor," or "sulfa-Michael donor," the electrophilic olefin is known as the "Michael acceptor," and the resultant reaction product of the two components is known as the "Michael adduct" and referred herein as the "sulfide-based compound." In some embodiments, the resultant sulfide-based compounds are used to inhibit corrosion of metal containments that contact fluids containing corrodents.

Below is the general scheme or Formula (A) of the sulfide-based compounds:

Formula A

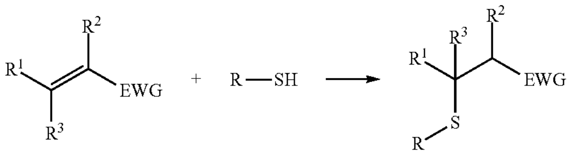

wherein $R^1$=H or CH3;

$R^2$=H or CH3, or an unsubstituted, linear or branched C2-C30 alkyl, alkenyl, or alkynyl group; In some embodiments, $R^2$=H or CH3, or an unsubstituted, linear or branched C2-C10 alkyl, alkenyl, or alkynyl group;

$R^3$=H or CH3

$R^1$, $R^2$, $R^3$=the same or different compounds having ethylenic unsaturations between carbon atoms at the α and β positions relative to a EWG group;

EWG=an electron withdrawing group that is ketone, halo, carbonyl (—CO), nitro ($-NO_2$), nitrile (—CN), alkoxycarbonyl (—COOR), phosphonate ($-PO(OR)_2$), trifluoromethyl ($-CF_3$), sulfonyl ($-SO_2-$), trifluormethanesulfonyl ($-SO_2CF_3$), or p-toluenesulfonyl ($-SO_2-C_6H_4-CH_3$); and R=straight, branched, cyclic or heterocyclic alkylene, arylene, alkylarylene, arylalkylene, or hydrocarbon moiety having from 1 to 30 carbon atoms.

In some embodiments, Formula A is used for corrosion inhibition. In some embodiments, a corrosion inhibitor composition comprises at least one sulfide-based compound, the at least one sulfide-based compound formed by a Michael addition reaction between a sulfa-Michael donor and an olefin as a Michael acceptor A "Michael donor," may be a compound with at least one Michael donor functional group, which is a functional group containing at least one sulfur-containing group or compound. In some embodiments, the Michael donor is a thiol or a sulfhydryl group (—SH). In some embodiments, the thiol group is a thiol (R—SH). A thiol can include at least one a sulfhydryl or thiol group monomer, or a reactive oligomer or reactive polymer or pre-polymer having at least one thiol group. Suitable thiol-containing compounds have one or more functional thiol groups and may be of any molecular weight. In some embodiments, the thiol monomer may be selected from one or more of aliphatic thiols, thiol glycolate esters, thiol propionate esters. In some embodiments, thiol-containing monomers include mercapto compounds.

Mercapto-compounds useful In some embodiments disclosed herein include chemicals containing at least one mercapto group. In some embodiments, mercapto-groups include mercapto-alcohols. In some embodiments, the mercapto-alcohols have the general formula (HS)n R—(OH)m, where R is a straight, branched, cyclic or heterocyclic alkylene, arylene, alkylarylene, arylalkylene, or hydrocarbon moiety having from 1 to 30 carbon atoms, and n and m each independently range from 1 to 3. In some embodiments, the mercapto-compounds include mercaptoethanol, 1-mercaptopropanediol (thioglycerol), 3-mercapto-2-butanol, 1-mercapto-2-propanol, 3-mercaptopropionic acid, mercaptoacetic acid, mercaptosuccinic acid, 2-mercaptophenol, 2-mercaptobenzoic acid, 3-mercapto-1-propanol, 2-mercaptobezoxazole, 2-mercaptobenzothiazole, 2-mercaptobenzoimidazole, 2-mercaptoimidazole, 2-mercapto-5-methylbenzimidazole, 2-mercaptonicotinic acid, mercaptopropyltrimethoxysilane, and 1-[(2-hydroxyethyl)thio]-3-(octyloxy)-2-propanol, 3-mercapto-1,2-propanediol (thioglycerol), 3-mercapto-2-butanol, 2-mercapto-3-butanol, 1-mercapto-2-propanol, 4-mercapto-4-methylpentan-2-ol, 3-mercapto-1-hexanol, 11-mercapto-1-undecanol, 6-mercapto-1-hexanol, 8-mercapto-1-octanol, 9-mercapto-1-nonanol, and combinations thereof.

In some embodiments the mercapto compounds are mercaptoalcohols. In some embodiments, the mercaptoalcohol is a 2 mercaptoethanol. In some embodiments the commercial mecapto compounds are 2-mercapto-1-methylimidazole, 2-mercapto-6-methylpyridine, 3-mercapto-2-butanone, mercapto glycolic benzoic acid, 3-mercapto-1-propanol, 1-mercapto-2-propanol, 2-mercapto-4(3H)-quinazolinone, 3-mercapto-3-methyl-1-butyl-1-formate, 3-mercapto-3-methylbutan-1-ol, and the like are all available from Sigma-Aldrich.

In some embodiments, the thiol-containing compound is pentaerythritol tetra(3-mercaptopropionate) (PETMP); 1-octanethiol; butyl 3-mercaptopropionate; 2,4,6-trioxo-1,3,5-triazina-trig (tricthyl-tris(3-mercapto propionate); 1,6-hexanedithiol; 2,5-dimercaptomethyl-1,4-dithiane, pentaerythritol tetramercaptoacetate, trimethylolpropane trimercaptoacetate, 2,3-dimercapto-1-propanol, 2-mercaptocthylsulfide, 2,3-(dimercaptoethylthio)-1-mercaptopropane, 1,2,3-trimercaptopropane, toluenedithiol, xylylenedithiol, 1,8-octanedithiol, 1-hexanethiol (Sigma-Aldrich, Milwaukee, Wis.); and trimethylolpropane tris(3-mercaptopropionate), and glycol dimercaptopropionate (Evans Chemetics LP, Iselin, N.J.).

A "Michael acceptor" refers to an alkene or olefin. In some embodiments an alkenyl group is proximate to an electron-withdrawing group (EWG) such as, for example, e.g., carbonyl, nitrile, sulfone, nitro, phosphonate. In some embodiments, the EWG is a ketone, halo, carbonyl (—CO), nitro ($-NO_2$), nitrile (—CN), alkoxycarbonyl (—COOR), phosphonate ($-PO(OR)_2$), trifluoromethyl ($-CF_3$), sulfonyl ($-SO_2-$), trifluormethanesulfonyl ($-SO_2CF_3$), or p-toluenesulfonyl ($-SO_2-C_6H_4-CH_3$). In some embodiments, the olefin is an α, β unsaturated compound such as ethylenic unsaturations between carbon atoms at the α and β positions relative (e.g. a carbonyl group.)

In some embodiments, a Michael acceptor group is a vinyl ketone, a vinyl sulfone, a quinone, an enamine, a ketimine, an aldimine, an oxazolidine, and an acrylate.

In some embodiments, Michael acceptors include acrylate esters, acrylonitrile, acrylamides, maleimides, alkyl methacrylates, cyanoacrylates, vinyl ketones, α,β-unsaturated aldehydes, vinyl phosphonates, acrylonitrile, vinyl pyridines, azo compounds, β-keto acetylenes, acetylene esters, nitro ethylenes, and the like. In some embodiments, a Michael acceptor group is derived from a vinyl sulfone and has the structure of Formula C $$-S(O)_2-CR=CH_2 \quad (C)$$

In some embodiments, anionic olefins are acrylic acid, methacrylic acid, itaconic acid, maleic acid, vinylsulfonic acid, vinylphosphonic acid, 2-acrylamido-2-methylpropane sulfonic acid (AMPS), 3-(allyloxy)-2-hydroxypropane-1-sulfonate, and the like.

In some embodiments, cationic olefins are (3-acrylamidopropyl) trimethylammonium chloride (APTAC), [3-(Methacryloylamino)propyl]trimethylammonium chloride (MAPTAC), 2-(acryloyloxy)-N,N,N-trimethylethanaminium chloride (DMAEA-MCQ), N,N-dimethylaminoethyl acrylate benzyl chloride quaternary salt (DMAEA-BCQ), 2-(methacryloyloxy)-N,N,N-trimethylethan-1-aminium methyl sulfate (DMAEA-MSQ), 2-(acryloyloxy)-N,N,N-trimethylethanaminium chloride (DMAEA-MSQ), and the like.

In some embodiments, non-ionic olefins are 4-vinylpyridine, 2-vinylpyridine, acrylate esters, alkyl methacrylates, acrylonitrile, acrylamides, and the like.

In some embodiments, the sulfide-based compounds are ammonium sulfides (structure I), sulfonate sulfides (structure II) and pyridine sulfides (Structure III):

I

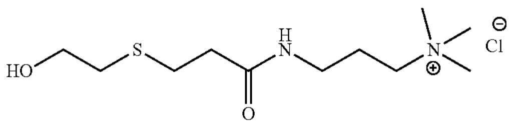

II

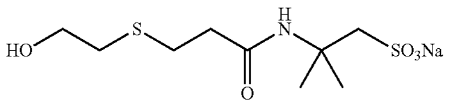

III

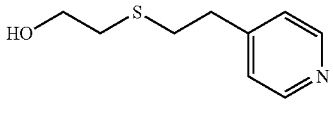

In some embodiments, structures I-III are used as corrosion inhibitors.

In some embodiments, the corrosion inhibitors are 3-(3-((2-hydroxyethyl)thio)propanamido)-N,N,N-trimethylpropan-1-aminium chloride; sodium 2-(3-((2-hydroxyethyl)thio)propanamido)-2-methylpropane-1-sulfonate; and 2-((2-(pyridin-4-yl)ethyl)thio)ethan-1-ol.

In some embodiments, the synthesis reaction schemes for preparation of sulfide-based chemistries are shown below:

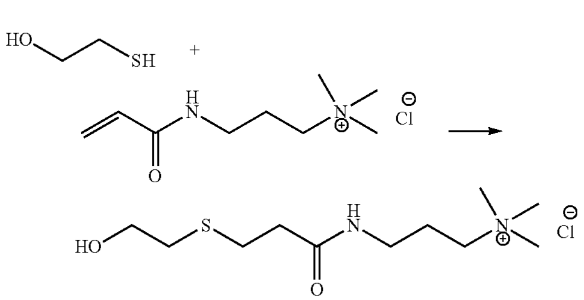

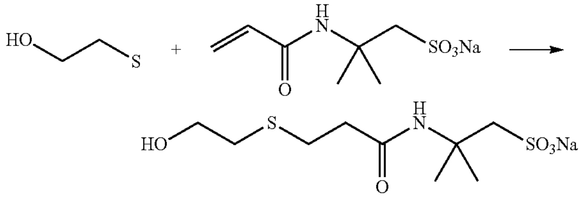

-continued

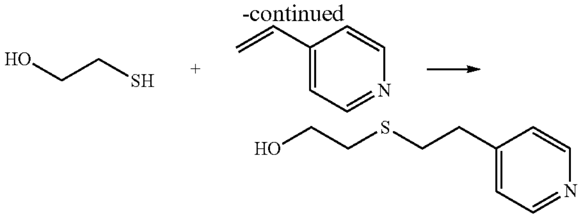

In some embodiments, the sulfide-based compounds are prepared with equimolar amounts of the Michael donor and Michael acceptor in the presence of a solvent and catalyst at temperatures in the range from 20° C.-80° C., 25° C.-50° C., 30° C.-60° C., 45° C.-75° C., or 50° C.-80° C. In some embodiments, the solvent used can be water, methyl phenol, chloroform, ethers (e.g., tetrahydrofuran (THF)), aromatic hydrocarbons (e.g., toluene and xylene), alcohols (e.g., n-butanol, methanol and ethanol), esters (e.g., ethyl 3-ethoxypropionate) and the like.

Other solvents include, but are not limited to, oxygenated solvents such as lower alkanols, lower alkyl ethers, glycols, aryl glycol ethers and lower alkyl glycol ethers. Examples of other solvents include, but are not limited to, propanol, isopropanol, isobutanol, ethylene glycol, diethylene glycol, triethylene glycol, propylene glycol, dipropylene glycol, hexylene glycol, mixed ethylene-propylene glycol ethers, ethylene glycol phenyl ether, and propylene glycol phenyl ether. The solvent used herein can be of a single solvent or a mixture of many different solvents.

In some embodiments, the reaction can be carried out solvent free. When a solvent is used, a wide range of solvents can be used for the reaction because the synthesis process is relatively insensitive to solvent. When solvent (or diluent) is used, the solvent can range from as low as about 1 wt-% up to about 80 wt-% and higher of the total composition. In some embodiments, the solvent is from about 1 wt-% to about 10 wt-%, from about 10 wt-% to about 20 wt-%, from about 20 wt-% to about 30 wt-%, from about 30 wt-% to about 40 wt-%, from about 40 wt-% to about 50 wt-%, from about 50 wt-% to about 60 wt-%, from about 60 wt-% to about 70 wt-%, from about 70 wt-% to about 80 wt-%, from about 1 wt-% to about 20 wt-%, from about 20 wt-% to about 40 wt-%, from about 40 wt-% to about 60 wt-%, from about 60 wt-% to about 80 wt-%, from about 40 wt-% to about 70 wt-%, about 5 wt-%, about 15 wt-%, about 25 wt-%, about 35 wt-%, about 45 wt-%, about 55 wt-%, about 65 wt-%, about 75 wt-% of the total composition.

In some embodiments, the catalysts used in the sulfa-Michael addition reaction are strong bases such as alkali metal alkoxides, hydroxides, and amines (e.g. butylamine). In some embodiments the catalyst is sodium pyrophosphate.

In some embodiments, the reaction time for the synthesis varies depending on factors such as the reaction temperature, the efficacy, and the catalyst amount, the presence or absence of diluent (solvent), and the like. In some embodiments, the reaction time is from about 10 minutes to about 48 hours, from about 0.5 hours to 48 hours, from about 1 hour to 40 hours, from about 2 hours to 38 hours, from about 4 hours to 36 hours, from 6 hours to 34 hours, from about 8 hours to 32 hours, from about 10 hours to 30 hours, from about 12 hours to 28 hours, from about 14 hours to 26 hours, from about 16 hours to 24 hours, from about 18 hours to 20 hours, from about 1 hour to 8 hours, from 8 hours to 16 hours, from about 8 hours to 24 hours, about 2 hours, about 4 hours, about 6 hours, about 8 hours, about 10 hours, about 14 hours, about 16 hours, about 18 hours, about 24 hours, about 30 hours, or about 36 hours.

Detecting the extent of the reaction and/or verifying the formation of a sulfide-based compound is accomplished using one or more common analytical methods known to those of skill in the art. In some embodiments such methods include liquid chromatography, gas chromatography, mass spectrometry, and thin layer chromatography.

The compositions and methods described herein are used to inhibit corrosion. In some embodiments, compositions comprise, consist essentially of, or consist of at least one of the described sulfide-based compound used for corrosion inhibition. In some embodiments, the sulfide-based compound or compositions containing them include other additives such as one or more asphaltene inhibitors, paraffin inhibitors, scale inhibitors, demulsifiers, water clarifiers, dispersants, emulsion breakers, antifoams, or any combination thereof. In some embodiments, the sulfide-based compound further comprises one or more solvents or a mixture thereof.

In some embodiments, a composition which includes solvents suitable for formulation of the sulfide-based compound are water, brine, seawater, alcohols such as methanol, ethanol, isopropanol, n-propanol, n-butanol, isobutanol, sec-butanol, t-butanol or higher alcohols such as benzyl alcohol); ketones such as acetone, or methyl ethyl ketone (2-butanone); acetonitrile; esters such as ethyl acetate, propyl acetate and butyl acetate; ethers such as diethyl ether or higher, e.g. methyl t-butyl ether, glyme, diglyme, ethylene glycol monobutyl ether, ethylene diglycol ethyl ether, 1,4 dioxane and related; aromatics such as toluene, xylene(s), diethylbenzene, naphthalene and related aromatics or refinery cuts (heavy aromatic naptha, heavy aromatic distillates, and related); aliphatics such as pentane, hexane, heptane, octane, or refined gasoline; or several "green" solvents such as 2-methyltetrahydrofuran, furfural alcohol, and cyclopentylmethylether.

In some embodiments, the solvents suitable for formulation with the sulfide-based composition are aliphatic, such as pentane, hexane, cyclohexane, methylcyclohexane, heptane, decane, dodecane, diesel, and the like, and aromatics, such as toluene, xylene, heavy aromatic naphtha, fatty acid derivatives (acids, esters, amides), and the like.

In some embodiments, the composition can include solvents disclosed in U.S. patent application Ser. No. 15/992,383 filed May 30, 2018 and incorporated herein by reference in its entirety.

In some embodiments, the solvents used to enhance the corrosion performance of the compositions containing the sulfide-based compounds are sulfur containing compounds. In some embodiments the other sulfur-containing compounds are, thioglycolic acid, 3,3'-dithiodipropionic acid, thiosulfate, thiourea, 2-mercaptoethanol, L-cysteine, and tert-butyl mercaptan.

In some embodiments the one or more solvents are 10 wt % to 99 wt % of the composition; 1-25 wt %, 20-50 wt %, 30-75 wt %, 50-75%, 75-100 wt % of the composition.

In some embodiments, the sulfide-based compounds are provided neat (viz., without a solvent). In some embodiments, the sulfide-based compounds further include dissolving or dispersing the sulfide-based compounds in water or water mixed with a water-soluble solvent before applying the sulfide-based. In some embodiments, the sulfide-based compounds are provided as a concentrate. In some embodiments the method includes applying a sulfide-based concentrate directly to a metal containment in an amount that results in 0.1 ppm to 10,000 ppm ppm (by weight or by volume) of the sulfide-based compounds in the fluid source. In other embodiments the method further includes diluting a sulfide-based compound concentrate prior to the introducing. The diluting comprises, consists essentially of, or consists of combining a sulfide-based compound concentrate with a diluent, wherein the diluent comprises, consists essentially of, or consists of water, a water source, a water soluble solvent, or a mixture of two or more thereof; and optionally includes mixing the sulfide-based compound concentrate with the diluent prior to the introducing of the sulfide-based compounds to the fluid source.

In some embodiments, the sulfide-based compounds or in a composition is used in a method of inhibiting corrosion in a fluid source. The fluid source can be contained in a metal container or in contact with pipelines used to transport fluid sources toward, into, out of a subterranean formation. In some embodiments, the fluid source contains corrodents. In some embodiments, the corrodents include hydrogen sulfide, carbon dioxide, oxygen, sodium chloride, calcium chloride, sulfur dioxide, or combination thereof. In some embodiments, the fluid source comprises water, gas, and optionally liquid hydrocarbon or combinations thereof. In some embodiments, the fluid source is produced water or an injectate. In some embodiments, the metal containment is a tank, pipe, or other apparatus having a metal surface in contact with a fluid source, or potentially in contact with a fluid source, wherein the fluid source includes one or more corrodents.

In some embodiments, the sulfide-based compounds inhibit corrosion of the metal surface more effectively than a conventional sulfur-based corrosion inhibitor.

In some embodiments, the pH of the fluid source is less than 7. In some embodiments, the pH of the fluid source is between about 1 and about 6, between 5 and 6, between 4 and 5, between 3 and 4, between 2 and 3, between 1 and 2, or between 0 and 1.

In some embodiments, various dosage amounts of the composition and/or the sulfide-based compound are introduced to a fluid source to inhibit corrosion of a metal containment in contact with the fluid source. One of ordinary skill in the art is able to calculate the amount of sulfide-based compound or composition comprising sulfide-based compound for a given situation without undue experimentation. Factors that would be considered important in such calculations include, for example, content of fluid source, content of corrodents, percentage water cut, and similar parameters.

In some embodiments, the composition comprising the sulfide-based compound is applied to a fluid source that contains various levels of water cut. One of ordinary skill in the art understands that "water cut" refers to the water percentage in a hydrocarbon phase (e.g. oil) and water mixture. In one embodiment, the water cut is from about 1% to about 80% w/w with respect to the hydrocarbon phase. In other embodiments, the water cut is from about 1% to about 30% w/w, from about 5% to about 40% w/w, from about 10% to about 60% w/w, from about 15% to about 80% w/w with respect to the hydrocarbon phase.

In some embodiments, the sulfide-based compounds or in a composition is applied to a fluid source that contains various levels of salinity. In one embodiment, the fluid source has a salinity of about 0.1% to about 25% or about 10% to about 25% weight/weight (w/w) total dissolved solids.

In some embodiments, the sulfide-based compounds or in a composition are used in an amount from about 0.1 ppm to 10,000 ppm; from about 100 ppm to 1000; from about 500 ppm to 3000 ppm; from about 750 ppm to 3,000 ppm; from about 5000 ppm to 2,000 ppm; from about 5000 ppm to 3,000 ppm; from about 100 ppm to 3,000 ppm; from about 1 ppm to 100 ppm, from about 10 ppm to 50 ppm; from about 50 ppm to 100 ppm, from about 1 ppm to 50 ppm; from about 1 ppm to 20 ppm; from about 1 ppm to 5 ppm; from about 3 ppm to 20 ppm; from 0.1 ppm to 5 ppm; or from about 0.1 ppm to 1 ppm by weight or volume of the sulfide-based compound in the fluid source.

In some embodiments, the sulfide-based compounds provides from about 50-99%, 75-99%, or 75-50% corrosion inhibition for containment in contact with a fluid source. In some embodiments, the sulfide-based compounds provides from about 50-99% corrosion protection for a containment in contact with a fluid source, as determined by a 1018 carbon steel coupon in a bubble test as described in Example 4. In some embodiments, the method provides at least 70% corrosion protection for a 1018 carbon steel coupon in a bubble test, from about 70-90%, 75-85% or 80-90% wherein the bubble test is characterized by a testing temperature of about 80° C.; a $CO_2$ saturated liquid medium of 100% brine; a test duration of 2-3 hours; and an corrosion inhibitor dosage of 25 ppm, 50 ppm, 75 ppm, 100 ppm, 200 ppm, 300 ppm, 400 ppm, 500 ppm, 1,000 ppm, 5,000, 7,500 ppm, or 15,000 ppm based on total fluids.

In some embodiments, the method provides at least 65% protection, from about 65-80%, 70-90%, 75-85% or 80-90% after two hours, at least 85% protection after 8 hours, and about 100% protection 10 hours.

In some embodiments, the sulfide-based compounds are more effective, on a weight basis, at inhibiting corrosion than at least one of 2-mercaptoethanol, thioglycolic acid, and sodium thiosulfate. In some embodiments, the sulfide-based compounds inhibit corrosion of the metal surface as effectively as 2-mercaptoethanol, on a weight basis. In some embodiments, the sulfide-based compounds inhibit corrosion of the metal surface more effectively than 2-mercaptoethanol, on a weight basis In some embodiments the sulfide-based compound is introduced into a fluid source by any means suitable for ensuring dispersal of the sulfide-based compound through the fluid source being treated. The composition comprising the sulfide-based compound can be injected as prepared or formulated in one or more additional solvents, depending upon the application and requirements. One of skill in the art will understand that the methods disclosed herein are not limited in any way by the introduction method, the timing or the location of the introduction.

In some embodiments, the sulfide-based compound is introduced to a fluid using various well-known methods and they may be introduced at numerous, different locations throughout a given system. In one embodiment, the composition comprising the sulfide-based chemistry is pumped into an oil/gas pipeline using an umbilical line. In some embodiments, capillary string injection systems may be utilized to deliver the composition. U.S. Pat. No. 7,311,144 provides a description of an apparatus and methods relating to capillary injection, the disclosure of which is incorporated into the present application in its entirety. In other embodiments, the composition comprising the one or more sulfide-based compound is injected using mechanical equipment such as chemical injection pumps, piping tees, injection fittings, and the like.

Introducing may be achieved also by mixing, blending with mechanical mixing equipment or devices, stationary mixing setup or equipment, magnetic mixing or other suitable methods, other equipment and means known to one skilled in the art and combinations thereof to provide adequate contact and/or dispersion of the composition into the fluid source. The contacting can be made in-line and/or offline. The various components of the composition may be mixed prior to and/or during contact. If needed or desired, the composition or some of its components may be optionally removed or separated mechanically, chemically, or by other methods known to one skilled in the art.

The sulfide-based compounds are also useful as corrosion inhibitors for other industrial systems. In some embodiments, the sulfide-based compounds are used in metallurgical industry, air conditioning and refrigeration systems, mining systems, water reclamation systems, water purification systems, food processing systems (meat, fruit and vegetable), waste treatment systems, municipal sewage and water treatment systems.

Below are described additional embodiments.

Embodiment 1. A composition comprising at least one sulfide-based compound, the at least one sulfide-based compound formed by a Michael addition reaction between a sulfa-Michael donor and an olefin as a Michael acceptor.

Embodiment 2. The composition of embodiment 1, wherein the sulfa-Michael donor comprises a sulfur-containing group or compound.

Embodiment 3. The composition as in one of embodiments 1-2, wherein the sulfa-Michael donor comprises a thiol or a sulfhydryl group (—SH).

Embodiment 4. The composition as in one of embodiments 1-3, wherein the sulfa-Michael donor comprises a mercaptoalcohol.

Embodiment 5. The composition as in one of embodiments 1-4, wherein the sulfa-Michael donor comprises mercaptoethanol.

Embodiment 6. The composition as in one of embodiments 1-5, wherein the olefin comprises α,β-unsaturated carbonyl compounds.

Embodiment 7. The composition as in one of embodiments 1-6, wherein the α,β-unsaturated carbonyl compounds comprises a vinyl ketone, a vinyl sulfone, a quinone, an enamine, a ketimine, an aldimine, an oxazolidine, and an acrylate, acrylate esters, acrylonitrile, acrylamides, maleimides, alkyl methacrylates, cyanoacrylates, vinyl ketones, α,β-unsaturated aldehydes, vinyl phosphonates, acrylonitrile, vinyl pyridines, azo compounds, β-keto acetylenes, acetylene esters, nitro ethylenes.

Embodiment 8. The composition as in one of embodiments 1-6, wherein the sulfide-based compound comprises:

I

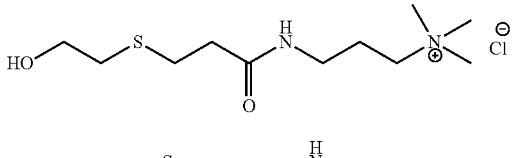

II

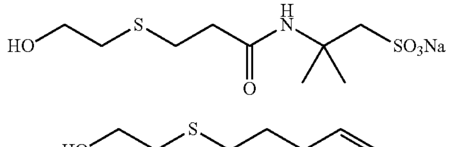

III

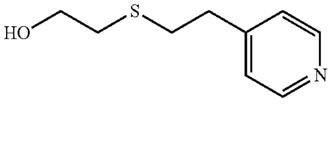

Embodiment 9. The composition as in one of embodiments 1-8, further comprising a solvent, wherein the solvent is present in the composition at about 10 wt % to 99 wt % of the composition.

Embodiment 10. The composition as in one of embodiments 1-9, wherein the composition further comprises one or more asphaltene inhibitors, paraffin inhibitors, scale inhibitors, demulsifiers, water clarifiers, dispersants, emulsion breakers, antifoams, or any combination thereof.

Embodiment 11. A fluid source comprising one or more corrodents and at least one sulfide-based compound as in one of embodiments 1-10.

Embodiment 12. The composition of embodiment 11, wherein the fluid source comprises produced water or injectate.

Embodiment 13. The composition as in one of embodiments 11-12, wherein the fluid source comprises water, gas, and optionally liquid hydrocarbon.

Embodiment 14. The composition as in one of embodiments 11-13, wherein the fluid source comprises about 0.1% to about 25% weight/weight total dissolved solids.

Embodiment 15. The composition as in one of embodiments 11-14, wherein the one or more corrodents comprise hydrogen sulfide, carbon dioxide, oxygen, sodium chloride, calcium chloride, sulfur dioxide, or a mixture of two or more thereof.

Embodiment 16. The composition as in one of embodiments 11-15, wherein the sulfide-based compound is about is about 0.1 ppm to 10,000 ppm by weight or volume of the composition.

Embodiment 17. The composition comprising a sulfide-based compound comprising the formula:

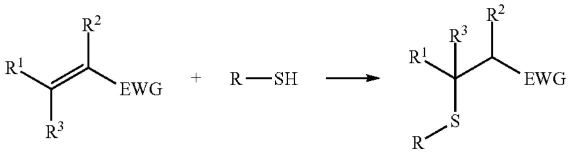

Wherein $R^1$=H or CH3;
- $R^2$=H, CH3, an unsubstituted, linear or branched C2-C30 alkyl, alkenyl, or alkynyl group;
- $R^3$=H or CH3
- $R^1$, $R^2$, $R^3$==the same or different compounds having ethylenic unsaturations between carbon atoms at the $\alpha$ and $\beta$ positions relative to a EWG group;
- EWG=an electron withdrawing group that is ketone, halo, carbonyl (—CO), nitro ($—NO_2$), nitrile (—CN), alkoxycarbonyl (—COOR), phosphonate ($—PO(OR)_2$), trifluoromethyl ($—CF_3$), sulfonyl ($—SO_2—$), trifluormethanesulfonyl ($—SO_2CF_3$), or p-toluenesulfonyl ($—SO_2—C_6H_4—CH_3$); and
- R=straight, branched, cyclic or heterocyclic alkylene, arylene, alkylarylene, arylalkylene, or hydrocarbon moiety having from 1 to 30 carbon atoms.

Embodiment 18. The composition as in embodiment 17, wherein the sulfide-based compound comprises:

I

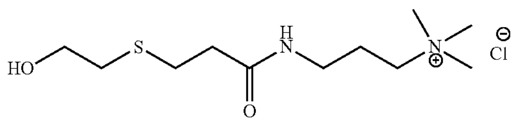

-continued

II

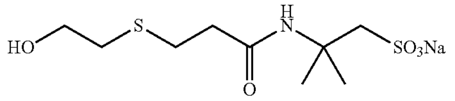

III

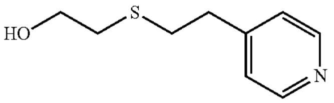

Embodiment 19. A method of inhibiting corrosion of metal containments in contact with a fluid source comprising the steps of:
- introducing into the fluid source a composition comprising at least one sulfide-based compound, the at least one sulfide-based compound formed by a Michael addition reaction between a sulfa Michael donor and an olefin Michael acceptor.

Embodiment 20. The method of embodiment 19, wherein introducing comprises by injecting or pumping.

Embodiment 21. The method of embodiment 19, wherein the fluid source is contained in an oil or gas pipeline or refinery.

Embodiment 22. The method as in one of embodiments 19-21, wherein the fluid source comprises water, gas, optionally liquid hydrocarbon or combination thereof.

Embodiment 23. The method as in one of embodiments 19-22, wherein the fluid source comprises about 0.1% to about 25% weight/weight total dissolved solids.

Embodiment 24. The method as in one of embodiments 19-23, wherein the fluid comprises water of about 1% to about 80% weight/weight with respect to the hydrocarbon phase.

Embodiment 25. The method as in one of embodiments 19-24, wherein the sulfide-based compound has the general formula:

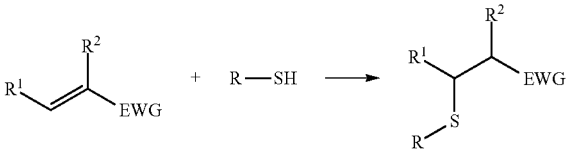

Wherein $R^1$=H or CH3;
- $R^2$=H, CH3, an unsubstituted, linear or branched C2-C30 alkyl, alkenyl, or alkynyl group;
- $R^3$=H or CH3
- $R^1$, $R^2$, $R^3$=the same or different compounds having ethylenic unsaturations between carbon atoms at the $\alpha$ and $\beta$ positions relative to a EWG group;
- EWG=an electron withdrawing group that is ketone, halo, carbonyl (—CO), nitro ($—NO_2$), nitrile (—CN), alkoxycarbonyl (—COOR), phosphonate ($—PO(OR)_2$), trifluoromethyl ($—CF_3$), sulfonyl ($—SO_2—$), trifluormethanesulfonyl ($—SO_2CF_3$), or p-toluenesulfonyl ($—SO_2—C_6H_4—CH_3$); and
- R=straight, branched, cyclic or heterocyclic alkylene, arylene, alkylarylene, arylalkylene, or hydrocarbon moiety having from 1 to 30 carbon atoms.

Embodiment 26. The method as in one of embodiments 19-25, wherein the sulfa-Michael donor comprises a sulfur-containing group or compound.

Embodiment 27. The method as in one of embodiments 19-26, wherein the sulfa-Michael donor comprises a thiol or a sulfhydryl group (—SH).

Embodiment 28. The method as in one of embodiments 19-27, wherein the sulfa-Michael donor comprises a mercaptoalcohol.

Embodiment 29. The method as in one of embodiments 19-28, wherein the sulfa-Michael donor comprises mercaptoethanol.

Embodiment 30. The method as in one of embodiments 19-29, wherein the olefins comprises α,β-unsaturated carbonyl compounds.

Embodiment 31. The method as in one of embodiments 19-30, wherein the α,β-unsaturated carbonyl compounds comprises a vinyl ketone, a vinyl sulfone, a quinone, an enamine, a ketimine, an aldimine, an oxazolidine, and an acrylate, acrylate esters, acrylonitrile, acrylamides, maleimides, alkyl methacrylates, cyanoacrylates, vinyl ketones, α,β-unsaturated aldehydes, vinyl phosphonates, acrylonitrile, vinyl pyridines, azo compounds, β-keto acetylenes, acetylene esters, nitro ethylenes.

Embodiment 32. The method as in one of embodiments 19-30, wherein the reaction product comprises:

I

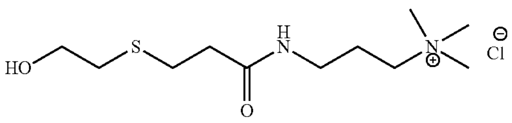

II

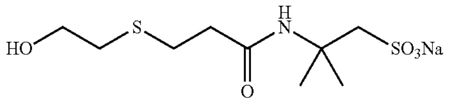

III

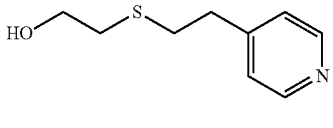

Embodiment 33. A treated metal containment comprising:

a metal containment comprising a metal surface; and the fluid source comprising the sulfide-based compound as in one of embodiments 19-32, wherein at least a portion of the metal surface is contacted by the fluid source.

Embodiment 34. The treated metal containment of embodiment 33, wherein the metal surface comprises carbon steel.

Embodiment 35. The treated metal containment as in one of embodiments 33-34, wherein the metal containment comprises a tank or pipe.

Embodiment 36. Use of the sulfide-based compound as in one of embodiments 1-35 to inhibit corrosion.

Embodiment 37. Use of the sulfide-based compound as in one of embodiments 1-35 to treat a fluid source comprising one or more corrodents.

Embodiment 38. Use of the sulfide-based compound as in one of embodiments 1-35 to inhibit corrosion of a metal containment comprising a fluid source comprising one or more corrodents.

EXAMPLES

The following examples are intended to illustrate different aspects and embodiments of the invention and are not to be considered limiting the scope of the invention. It will be recognized that various modifications and changes may be made to the experimental embodiments described herein and without departing from the scope of the claims.

Example 1: Preparation of 3-(3-((2-hydroxyethyl)thio)propanamido)-N,N,N-trimethylpropan-1-aminium chloride (Sample 1)

Butylamine (0.1 g, 0.001 mole) was added to a stirred mixture of 2-mercaptoethanol (1.55 g, 0.02 mol) and (3-acrylamidopropyl) trimethylammonium chloride (APTAC) (75%, 5.65 g, 0.02 mol) at ambient temperature. The resulting mixture was then stirred for 5 hours. The resulting aqueous solution of sulfide-based compound is used as is. Mass spectrometry (+ESI-MS) confirmed synthesis of sample 1: calc. [M−Cl−]+ 249.16, found 249.1612.

TABLE 1

| I | MW (g/mol) | Purity | Amount (g) | n (moles) | mole ratio |
|---|---|---|---|---|---|
| Mercaptoethanol | 78.13 | 99% | 1.55 | 0.02 | 1.00 |
| APTAC | 206.12 | 75% | 5.65 | 0.02 | 1.05 |
| Butylamine | 73.14 | | 0.1 | 0.001 | 0.07 |

Example 2: Preparation of sodium 2-(3-((2-hydroxyethyl)thio)propanamido)-2-methylpropane-1-sulfonate (Sample 2)

Butylamine (0.3 g, 0.004 mole) was added to a stirred mixture of 2-mercaptoethanol (1.55 g, 0.02 mol) and 2-acrylamido-2-methyl-1-propanesulfonic acid sodium salt solution in water (NaAMPS) (58%, 32.41, 0.02 mol) at ambient temperature. The resulting mixture was stirred at for 5 hours. The resulting aqueous solution of sulfide chemistry is used as is. Mass spectrometry (−ESI-MS) confirmed synthesis of sample 2: calc. [M−Na+]− 284.06, found 284.06300.

TABLE 2

| II | MW (g/mol) | Purity | Amount (g) | n (moles) | mole ratio |
|---|---|---|---|---|---|
| Mercaptoethanol | 78.13 | 99% | 6.21 | 0.08 | 1.00 |
| NaAMPS | 229.23 | 58% | 32.41 | 0.08 | 1.04 |
| Butylamine | 73.14 | | 0.3 | 0.004 | 0.05 |

Example 3: Preparation of 2-((2-(pyridin-4-yl)ethyl) thio)ethan-1-ol (Sample 3)

Butylamine (0.34 g, 0.005 mole) was added to a stirred mixture of 2-mercaptoethanol (13.89 g, 0.18 mol), water (10 g), and 4-vinylpyridine (95%, 21, 0.19 mol) at ambient temperature. The resulting mixture was stirred for 5 hour. The resulting aqueous solution of sulfide chemistry is used as is. Mass spectrometry (+ESI-MS) confirmed synthesis of sample 3: calc. [M+H]+ 184.08, found 184.0786.

TABLE 3

| III | MW (g/mol) | Purity | Amount (g) | n (moles) | mole ratio |
|---|---|---|---|---|---|
| Mercaptoethanol | 78.13 | 99% | 13.89 | 0.18 | 1.00 |
| 4-vinylpyridine | 105.14 | 95% | 21 | 0.19 | 1.08 |
| Butylamine | 73.14 | | 0.34 | 0.005 | 0.03 |
| Water | | | 10 | | |

Example 4: Corrosion Testing

The bubble cell test was used to investigate the effectiveness of the sulfide-based chemistries as corrosion inhibitors. This test measures the corrosion rate of a steel electrode by aqueous linear polarization resistance (LPR). The steel electrodes (C1018) were placed in in a bath of brine which was deaerated with carbon dioxide. The corrosion rate of the electrode was compared in the absence or presence of the sulfide-based chemistries.

The brine contained about 3 wt % of sodium chloride. The brine was placed into bubble cells and purged with $CO_2$. The brine was continually purged with $CO_2$ to saturate the brine prior to starting the test. The test cells were blanketed with $CO_2$ throughout the duration of the test to maintain saturation. The bubble cells were stirred at 100 revolutions per minute (rpm) for the duration of the test to maintain thermal equilibrium at 80° C.

After 2-3 hours of pre-corrosion time (i.e. with no corrosion inhibitor or sulfide-based chemistry) 25 ppm of a 20% active of quaternary ammonium sulfide (sample 1), sulfonate sulfide (sample 2), or pyridine sulfide (sample 3) in methanol solvent were added. Comparison with known sulfur containing inhibitor species, 2-mercaptoethanol (2ME), at the same active dose was made. A low concentration of 2-mercaptoethanol was used to differentiate between the tested chemistries. The inhibited corrosion rate after about 7 hours of chemical injection was taken and compared with samples before injection.

Table 4 shows a corrosion rate after three hours after the corrosion inhibitor was injected into the test.

TABLE 4

| Samples | Candidate Chemistry | Candidate Chemistry Activity (%) | Dosage (ppm) | Avg. Baseline Corrosion Rate (mpy) | 7 h after dosing: Inhibited Corrosion Rate (mpy) | 7 h after dosing: % Inhibition Protection |
|---|---|---|---|---|---|---|
| Comparative sample | 2 Mercaptoethanol | 20 | 25 | 221 | 232 | −5 |
| Sample 1 | Quaternary ammonium sulfide | 20 | 25 | 317 | 68 | 79 |
| Sample 2 | Sulfonate sulfide | 20 | 25 | 262 | 88 | 66 |
| Sample 3 | Pyridine sulfide | 20 | 25 | 272 | 85 | 69 |

The corrosion rate of the electrode was reduced from about 320 mpy to about 70 mpy when using the quaternary ammonium sulfide (Sample 1) resulting in about a 79% corrosion inhibition protection. The untreated electrode was reduced from about 260 mpy to about 90 mpy using the sulfonate sulfide (Sample 2) resulting in about a 66% corrosion inhibition protection. The untreated electrode was reduced from about 270 mpy to about 85 mpy when using the pyridine sulfide (Sample 3) resulting in about a 69% corrosion inhibition protection. All of the sulfide-based chemistries significantly outperformed that of the Comparative sample (2ME) in which the corrosion rate actually increased from about 220 mpy to about 230 mpy resulting in a negative corrosion inhibition protection.

What is claimed is:

1. A corrosion inhibition composition comprising at least one cationic or anionic sulfide-based compound comprising an OH group and a quaternary ammonium group or a sulfonate group, the at least one sulfide-based compound formed by a Michael addition reaction between a sulfa-Michael donor and a Michael acceptor comprising a carbon-carbon double bond, wherein the sulfa-Michael donor comprises a mercaptoalcohol, and wherein the Michael acceptor comprises an anionic sulfonate group or a cationic quaternary ammonium group.

2. The composition of claim 1 wherein the Michael acceptor comprises one or more nitrogen, sulfur, phosphorus, or halo atoms.

3. The composition of claim 1, wherein the Michael acceptor comprises an α,β-unsaturated carbonyl compound.

4. The composition of claim 1, wherein the sulfa-Michael donor comprises a mercaptoalcohol selected from the group consisting of mercaptoethanol, 1-mercaptopropanediol (thioglycerol), 1-mercapto-2-propanol, 3-mercapto-1-propanol, 3-mercapto-2-butanol, 2-mercapto-3-butanol, 3-mercapto-1-hexanol, 6-mercapto-1-hexanol, 8-mercapto-1-octanol, 9-mercapto-1-nonanol, 11-mercapto-1-undecanol, 2-mercaptophenol, 3-mercapto-3-methylbutan-1-ol, and 2,3-dimercapto-1-propanol.

5. The composition of claim 1, wherein the sulfa-Michael donor comprises a thiol or a sulfhydryl group (—SH).

6. The composition of claim 1, further comprising a solvent, wherein the solvent is present in an amount in the range of 10% (wt) to 99% (wt) of the composition.

7. The composition of claim 1, wherein the sulfide-based compound is present in an amount in the range of 0.1 ppm to 10,000 ppm in the composition.

8. A fluid-containing composition comprising a fluid, one or more corrodents, and the corrosion inhibition composition of claim 1.

9. The fluid-containing composition of claim 8, wherein the one or more corrodents is or are hydrogen sulfide, carbon dioxide, oxygen, sodium chloride, calcium chloride, sulfur dioxide, or a combination thereof.

10. The fluid-containing composition of claim 8 comprising water, gas, and optionally liquid hydrocarbon, or combinations thereof.

11. The fluid-containing composition of claim 8 comprising an amount of dissolved solids in the range of 0.1% to 25% weight/weight total dissolved solids.

12. The corrosion inhibition composition of claim 1, wherein the olefin as a Michael acceptor comprises an amide group.

13. The corrosion inhibition composition of claim 12, wherein the Michael acceptor is cationic and comprises an ammonium group.

14. The corrosion inhibition composition of claim 12, wherein the Michael acceptor is anionic and comprises a sulfonate group.

15. The corrosion inhibition composition of claim 1, wherein the at least one sulfide-based compound has the formula $HO—CH_2CH_2—S—CH_2CH_2—C(O)—NH—CH_2CH_2CH_2\text{-}QA$, wherein QA comprises an ammonium group.

16. The corrosion inhibition composition of claim 15, wherein the at least one sulfide-based compound has the formula

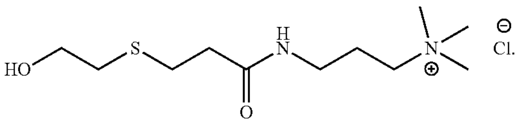 [SMILES: C[N+](C)(C)CCCNC(=O)CCSCCO]

17. The corrosion inhibition composition of claim 1, wherein the at least one sulfide-based compound has the formula $HO—CH_2CH_2—S—CH_2CH_2—C(O)—NH—C(CH_3)_2—CH_2—SA$, wherein SA comprises a sulfonate group.

18. The corrosion inhibition composition of claim 17, wherein the at least one sulfide-based compound has the formula

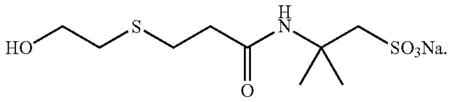

* * * * *